US00PP22090P3

(12) United States Plant Patent
Pen-chih

(10) Patent No.: US PP22,090 P3
(45) Date of Patent: Aug. 23, 2011

(54) ***PHALAENOPSIS* PLANT NAMED 'TAIDA LITTLE ZEBRA'**

(50) Latin Name: ***Phalaenopsis* hybrid**
Varietal Denomination: Taida Little Zebra

(76) Inventor: Lai Pen-chih, Chang-Hwa (TW)

( * ) Notice: Subject to any disclaimer, the term of this patent is extended or adjusted under 35 U.S.C. 154(b) by 0 days.

(21) Appl. No.: 12/592,550

(22) Filed: Nov. 27, 2009

(65) Prior Publication Data

US 2011/0131693 P1 Jun. 2, 2011

(51) Int. Cl.
*A01H 5/00* (2006.01)

(52) U.S. Cl. ..... Plt./311

(58) Field of Classification Search ..... Plt./311
See application file for complete search history.

*Primary Examiner* — June Hwu

(57) ABSTRACT

A new and distinct *Phalaenopsis* hybrid cultivar named 'TAIDA LITTLE ZEBRA' is disclosed, characterized by unique coloration of the petals and overall small, compact plant habit. The new variety is a *Phalaenopsis*, and is normally used as an ornamental plant.

1 Drawing Sheet

Figure 1:
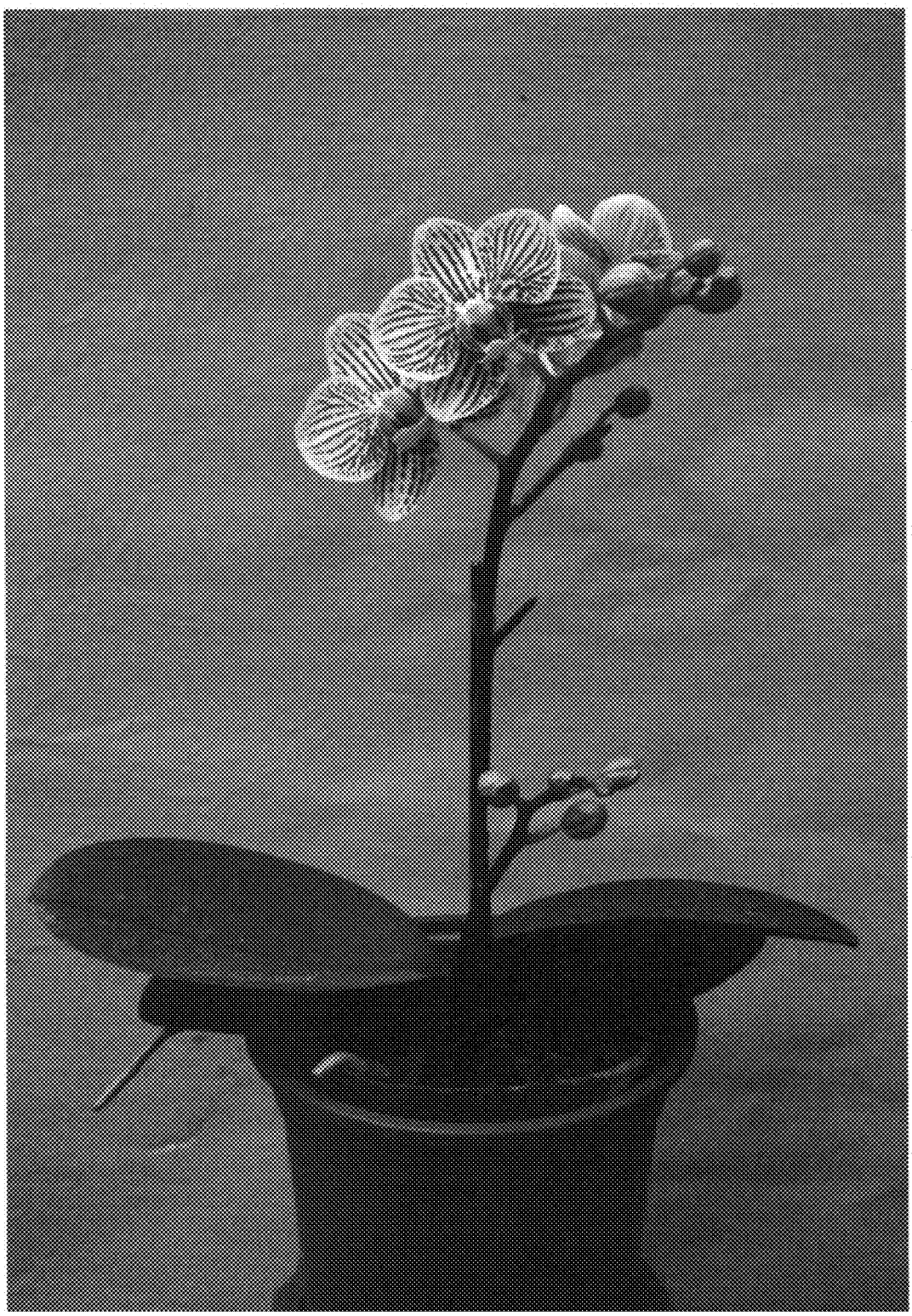

Latin name of the genus and species: *Phalaenopsis* hybrid.
Variety denomination: 'TAIDA LITTLE ZEBRA'.

BACKGROUND OF THE INVENTION

The new cultivar was discovered as part of a commercial breeding program, carried out in a commercial greenhouse in Chang-Hwa, Taiwan. The inventor, Lai Pen-chih, a citizen of Taiwan, discovered the new variety as the result of the crossing of the female parent, the unpatented variety *Phalaenopsis* hybrid 'Ho's Little Caroline' with the male parent, the unpatented variety *Phalaenopsis* hybrid 'Ever-Spring King.' The crossing was performed in April 2006, the new variety was discovered in May 2006 by the inventor.

Asexual reproduction of the new cultivar 'TAIDA LITTLE ZEBRA' by tissue culture was performed at a commercial laboratory in Chang-Hwa, Taiwan in 2006. Since that time, many generations have been reproduced, and have shown that the unique features of this cultivar are stable and reproduced true to type through successive generations.

SUMMARY OF THE INVENTION

The cultivar 'TAIDA LITTLE ZEBRA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TAIDA LITTLE ZEBRA.' These characteristics in combination distinguish 'TAIDA LITTLE ZEBRA' as a new and distinct *Phalaenopsis* hybrid cultivar:

1. Highly compact overall plant.
2. Unique white and purple bloom coloration.
3. Rough sepal and petal texture.

PARENT COMPARISON

Plants of the new cultivar 'TAIDA LITTLE ZEBRA' are similar to plants of the seed parent variety unpatented *Phalaenopsis* hybrid 'Ho's Little Caroline' in most horticultural characteristics. However, plants of the new cultivar 'TAIDA LITTLE ZEBRA' produce rough sepals and petals compared to smooth sepals and petal in the seed parent. Additionally, plants of 'TAIDA LITTLE ZEBRA' produce white flowers with purple stripes and spots, whereas 'Ho's Caroline' produces white flowers with pink spots.

Plants of the new cultivar 'TAIDA LITTLE ZEBRA' are similar to plants of the pollen parent variety, unpatented *Phalaenopsis* hybrid 'Ever-Spring King' in most horticultural characteristics. However, plants of the new cultivar 'TAIDA LITTLE ZEBRA' produce white flowers with purple stripes and spots, whereas 'Ever-Spring King' produces cream colored flowers with brown brindle.

COMMERCIAL COMPARISON

The most similar commercial variety, outside of the parent varieties is *Phalaenopsis*'Little Gem Stripe Lee'. 'TAIDA LITTLE ZEBRA' and 'Little Gem Stripe Lee 23' are similar in some horticultural characteristics, including over all short plant habit. However, 'TAIDA LITTLE ZEBRA' is shorter. Additionally, 'TAIDA LITTLE ZEBRA' has a stable and consistent color pattern to the flower, whereas 'Little Gem Stripe Lee 23' does not have a consistent color pattern on the flower. A search by the inventor does not reveal any other highly dwarf, stable white and purple *Phalaenopsis* varieties for comparison.

BRIEF DESCRIPTION OF THE PHOTOGRAPH

The accompanying photograph in FIG. 1 illustrates in full color a typical plant of 'TAIDA LITTLE ZEBRA' grown in a greenhouse. The pot size is a commercial 11 cm container. The plant shown is approximately 2 years old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'TAIDA LITTLE ZEBRA' plants grown in a commercial greenhouse in Chang-Hwa, Taiwan. Temperature ranged from 20° C. to 35° C. day and from 18° C. to 20° C. night. Light levels ranged from 10,000 lux as a young plant to approximately 20,000 lux for a flowering plant. Plants described began flowering in the Fall. Measurements and numerical values represent averages of typical flowering types. No chemical or photoperiodic treatments were given.

Botanical classification: *Phalaenopsis* hybrid 'TAIDA LITTLE ZEBRA.'

PROPAGATION

Type of propagation typically used: Tissue culture

Time to initiate roots: About 40 days at approximately 28-32° C.

Time to produce a rooted cutting/liner: About 5-6 months after cloning at approximately 28-35° C.

Root description: Thick (typical for *Phalaenopsis*) and rounded, average diameter: 5 mm, colored near RHS Greyed-Green 194C.

PLANT

Growth habit: Monopodial

Height from to of soil line to top of foliage: Average 11.9 cm

Height from to of soil line to top of flowers: Average 36.7 cm

Plant spread: At widest, average: 30.6 cm; at narrowest: 10.4 cm

Normal pot size: 11 cm

Growth rate: Moderate

Number of Leaves per plant: Average 8

FOLIAGE

Leaf:

*Arrangement.*—Distichous.

*Average length.*—Approximately 14.2 cm.

*Average width.*—Approximately 8.8 cm.

*Shape of blade.*—Obovate.

*Aspect.*—Horizontal.

*Apex.*—Unequal acute.

*Base.*—Cuneate. Sheath length: Average 1.2 cm. Sheath width: Average 1.8 cm. Sheath color: Near RHS Yellow-Green 147B closest to base, 147C near top of sheath.

*Margin.*—Entire.

*Texture of top surface.*—Smooth, glossy, slightly furrowed.

*Texture of bottom surface.*—Smooth, glossy, slightly furrowed.

Color.—Young foliage upper side: Near RHS Green N137A. Young foliage under side: Near RHS Yellow-Green 148A. Mature foliage upper side: Near RHS Green N137A. Mature foliage under side: Near RHS Yellow-Green 147B, tinged Brown N200B.

*Venation.*—Type: Camptodromous. Venation coloration: upper side near RHS Green N137A, under side near RHS Yellow-Green 147B, tinged Brown N200B, main vein on under side near RHS Greyed-Orange 177A near base, 177B towards apex.

Petiole: No petioles present

FLOWERING CHARACTERISTICS

General description: Typical *Phalaenopsis* flower in shape of inflorescence and individual flower Flower bud:

*Rate of opening.*—Flower is fully opened after 7 days from the bud stage described herein.

*Length.*—Approximately 1.5 cm.

*Diameter.*—Approximately 1.1 cm wide and 1.3 cm high.

*Shape.*—Broad ovate.

*Color.*—Near RHS Yellow-Green 145D, striped near Greyed-Red 182B.

Peduncle:

*Length.*—Approximately 34.7 cm.

*Width.*—Approximately 0.4 cm.

*Aspect.*—Approximately 70° angle to rosette.

*Strength.*—Strong.

*Texture.*—Smooth, not very glossy.

*Color.*—In between near RHS Green N137D and Yellow-Green 147A but darker. No anthocyanin coloration present.

INFLORESCENCE

*Flowers per stem.*—Average 20.

*Inflorescence arrangement.*—Panicle.

*Inflorescence height.*—Approximately 21.4 cm (measured from lowest flower to top of inflorescence.

*Inflorescence width.*—Approximately 18.6 cm.

INDIVIDUAL FLOWERS

Flower type: Typical *Phalaenopsis*-flower

*Shape.*—Zygomorphic.

*Length* (*height*).—Approximately 4.7 cm, excluding sheath.

*Width.*—Approximately 5.5 cm.

*Depth.*—Approximately 2.6 cm.

*Fragrance.*—No fragrance.

*Persistent.*—Non-persistent.

*Quantity of petals.*—2.

Petals:

*Arrangement.*—One petal on each side of the column. Very slightly overlapping.

*Length.*—Approximately 2.6 cm.

*Width.*—Approximately 2.9 cm.

*Shape.*—Reniform.

*Apex.*—Rounded.

*Base.*—Broad attenuate.

Margin.—Entire.

*Texture.*—Upper forward surface: rough, dull, somewhat velvety.

*Texture.*—Lower back surface: rough, somewhat velvety.

*Color.*—When opening, forward surface: Near RHS White N155C. When opening, back surface: Near RHS White N155D. Fully Opened, forward surface: Near RHS White N155D. Fully Opened, back surface: Near RHS White N 155D. Fading, forward surface: Near RHS Purple N78C. Fading, back surface: Near RHS Purple 77B.

*Color venation fully opened, forward surface.*—Near RHS Red-Purple 71A and Purple N79C, both colors present.

*Color venation fully opened, back surface.*—Near RHS Purple 77B.

Lip apical and lateral description:

*Lip apical lobe diameter.*—Approximately 1.5 cm.

*Lip apical lobe length.*—Approximately 1.2 cm.

*Lip Lateral lobe diameter.*—Approximately 0.4 cm.

*Lip Lateral lobe length.*—Approximately 0.9 cm.

*Lip apical lobe shape.*—Broad deltate, with conspicuous notches at apex.
*Lip lateral lobe.*—Flattened, shortened. oblong.
*Lip lateral lobe curvature.*—Very slight, cupped curvature.
*Whiskers.*—Absent.

Labellum:
*Shape.*—Three-parted.
*Length.*—Approximately 2.4 cm.
*Width.*—Approximately 2.7 cm.
*Texture.*—Smooth, dull, somewhat velvety.
*Tip.*—Emarginate.
*Base.*—Cuneate.
*Color.*—When opening, forward surface: central lobe near RHS Red-Purple 71A, light color towards the tip; Purple N78C, lateral lobes Purple N78B and N78C to 71B, base of each lobe Yellow 4C, with a dark blotch near Red-Purple 59A. No callosities present. When opening, back surface: Near RHS Purple 76C, margins Red-Purple 72B. Fully Opened, forward surface: Central lobe near RHS Red-Purple 71A, colored lighter towards the tip; near Purple N78C, lateral lobes near Purple N78B and N78C to Red-Purple 71B, base of each lobe near Yellow 4C, with a dark blotch; near Red-Purple 59A. No callosities present. Fully Opened, back surface: Near Purple 76C and 76D, both colors present. Margins 72B. Fading, forward surface: Central lobe near Red-Purple 59B, more violet towards the tip; near Purple-Violet N80A, lateral lobes near Purple-Violet N81A to Red-Purple 71A, base of each lobe Red-Purple 63B, with a dark blotch near Red-Purple 59A. Fading, back surface: Near RHS Red-Purple 70A.
*Color venation fully opened, forward surface.*—Near RHS Red-Purple 71A.
*Color venation fully opened, back surface.*—Not present.
*Margin.*—Entire.

Sepals:
*Quantity.*—3.
*Appearance.*—Rough, dull, somewhat velvety.
*Length.*—Approximately 2.9 cm.
*Width.*—Approximately 2.1 cm.
*Shape.*—Ovate to broad elliptic.
*Apex.*—Obtuse to broad bluntly acute.
*Base.*—Broad cuneate
*Margin.*—Entire.
*Texture.*—Smooth, dull, somewhat velvety.
*Color.*—Near RHS White N155 D, veined near RHS Purple N79C.

Pedicels:
*Length.*—Approximately 3.2 cm.
*Diameter.*—Approximately 0.3 cm.
*Angle.*—About 70 degrees.
*Strength.*—Moderately strong.
Texture.—Smooth, moderately glossy.
*Color.*—Near RHS Yellow-Green 145C, distal part lighter; near Green-White 157D.

REPRODUCTIVE ORGANS

*Stamens, style and stigma fused into column?.*—Yes.
*Column length.*—Approximately 0.9 cm.
*Column diameter.*—Approximately 0.5 cm.
*Column color.*—Near RHS Purple 76B.
*Ovary.*—Position: inferior. Diameter: Approximately 0.3 cm. Color: Near RHS Green-White 157D.
*Pollinia color.*—Near RHS Yellow-Orange 21A.

OTHER CHARACTERISTICS

Disease resistance: Neither resistance nor susceptibility to diseases or pests normal to *Phalaenopsis* has been observed in this variety.

Fruit/seed production: Not detected to date

What is claimed is:

1. A new and distinct cultivar of *Phalaenopsis* plant named 'TAIDA LITTLE ZEBRA' as herein illustrated and described.

* * * * *